United States Patent [19]

Beatty et al.

[11] Patent Number: 4,704,284

[45] Date of Patent: Nov. 3, 1987

[54] LONG-ACTING MATRIX TABLET FORMULATIONS

[75] Inventors: Morgan L. Beatty, Waterford; Wayne A. Boettner, Mystic, both of Conn.

[73] Assignee: Pfizer Inc., New York, N.Y.

[21] Appl. No.: 407,511

[22] Filed: Aug. 12, 1982

[51] Int. Cl.$^4$ ............................................. A61K 9/26
[52] U.S. Cl. .................................................... 421/469
[58] Field of Search ..................................... 424/19–22, 424/35, 36, 38, 469

[56] References Cited

U.S. PATENT DOCUMENTS

| | | | |
|---|---|---|---|
| 2,793,979 | 5/1957 | Svedrea et al. | 167/82 |
| 2,809,917 | 10/1957 | Hermelin | 424/21 |
| 2,951,792 | 9/1960 | Swintosky | 424/21 |
| 2,953,497 | 9/1960 | Press | 424/20 |
| 2,956,926 | 10/1960 | Grief | 424/38 |
| 2,987,445 | 6/1961 | Levesque | 167/82 |
| 2,993,836 | 7/1961 | Nash et al. | 167/82 |
| 3,039,933 | 6/1962 | Goldman | 167/82 |
| 3,044,938 | 7/1962 | Halley | 424/19 |
| 3,087,860 | 4/1963 | Endicott | 167/82 |
| 3,115,441 | 12/1963 | Hermelin | 424/38 |
| 3,317,394 | 5/1967 | Fryklof et al. | 424/22 |
| 3,322,633 | 6/1967 | Simoons | 167/82 |
| 3,336,200 | 8/1967 | Krause et al. | 424/19 |
| 3,344,029 | 9/1967 | Berger | 424/19 |
| 3,400,197 | 9/1968 | Lippmann | 424/21 |
| 3,577,514 | 5/1971 | Robinson | 424/22 |
| 3,608,063 | 9/1971 | Banker | 424/19 |
| 3,632,739 | 1/1972 | Kornbloom | 424/19 |
| 3,906,086 | 9/1975 | Guy et al. | 424/19 |
| 3,939,259 | 2/1976 | Pescetti | 424/19 |
| 3,978,203 | 8/1976 | Wise | 424/19 |
| 4,012,498 | 3/1977 | Kornblum et al. | 424/19 |
| 4,083,949 | 4/1978 | Benedikt | 424/35 |
| 4,122,157 | 10/1978 | Huber | 424/19 |
| 4,130,647 | 12/1978 | Taylor | 424/251 |
| 4,171,363 | 10/1979 | Crenshaw et al. | 424/251 |
| 4,343,789 | 8/1982 | Kawata et al. | 424/78 |
| 4,361,545 | 11/1982 | Powell et al. | 424/22 |
| 4,361,546 | 11/1982 | Stricker et al. | 424/22 |
| 4,367,217 | 1/1983 | Gruber et al. | 424/22 |

FOREIGN PATENT DOCUMENTS 1233055  5/1971  United Kingdom .................. 424/19

OTHER PUBLICATIONS

Eisai, Chem. Abstracts, 96, #11678k, (1982), of Jpn. Kokai, Tokyo Koho JP 81,122,311, Sep. 25, 1981, Sustained-Release Theophylline Formulations.

Lippol et al., Chem. Abstracts, 97, #133y72e, (1982), of Pharm. Ind., (1982), 44(7): 735–740, Dev. Prodn. Peroral Depot Prepn. with Constant Release Rates . . . Theophylline.

Nikken, Chem. Abstracts, 94, #90363p, (1981), of Jpn. Kokai Tokkyo Koho, 80,153,715, May 18, 1979, Slow-Release Theophylline Pills.

Kawata et al., Chem. Abstracts, 94, #127383y, (1981), Ger. Offen., 3,024,858, Jan. 22, 1981, Continuosly Releasing Pharmaceutical Propn. of A Solid Drug Material.

*Primary Examiner*—Shep K. Rose
*Attorney, Agent, or Firm*—Peter C. Richardson; Albert E. Frost; James M. McManus

[57] ABSTRACT

A pharmaceutical tablet which releases an initial burst of therapeutic agent and thereafter releases the agent at an essentially constant rate comprising an acid soluble therapeutic agent in an insoluble matrix, the tablet containing an acid insoluble, base soluble pharmaceutically acceptable component selected from polymers and fatty acids, a pharmaceutically acceptable organic acid and at least one pharmaceutically acceptable excipient, the component and the acid each being present in an amount of from about 1–25 percent by weight of the total composition.

6 Claims, No Drawings

LONG-ACTING MATRIX TABLET FORMULATIONS

BACKGROUND OF THE INVENTION

The present invention is concerned with long-acting matrix tablet formulations which release an initial burst of therapeutic agent and thereafter release the agent at an essentially constant rate. In particular, this invention is concerned with a matrix tablet specifically designed to release an initial burst of acid soluble therapeutic agent into the stomach and then to release agent at a constant rate into the stomach and/or small intestine thereafter.

Numerous matrix systems have been devised which perform similar tasks but each suffers from some disadvantage. For example, waxes and lipids have often been used in matrix tablet formulations as described in U.S. Pat. Nos. 2,793,979 and 2,993,836. Ethylcellulose has been used in matrix formulations with polyethylene glycol (U.S. Pat. No. 3,039,933) with calcium stearate (U.S. Pat. No. 3,322,633) and with calcium sulfate (U.S. Pat. No. 3,632,739) among other ingredients. Other known matrix materials include carboxymethylcellulose, cellulose acetate phthlate, sodium carboxymethylcellulose, gums, carbohydrates such as starch and sorbitol, etc.

Still another class of matrix tablets makes use of polymeric matrix materials. U.S. Pat. No. 3,087,860 teaches the use of methyl acrylate—methyl methacrylate and U.S. Pat. No. 2,987,445 teaches the use of various polymers and copolymers such as polyethylene, polymethyl methacrylate and copolymers of methyl methacrylate and alkyl acrylates and the like.

All of these various matrix formulations suffer from disadvantages. The primary disadvantage is slowing of the release rate as a function of time. Other disadvantages include dumping of entire dose in the stomach, short life in the gastrointestinal tract, difficulty of manufacture, the inclusion undesireable ingredients, etc. The present invention for the first time presents a safe, easy-to-make, long-acting matrix tablet formulation especially suited for acid soluble therapeutic agents.

SUMMARY OF THE INVENTION

The present invention comprises a pharmaceutical tablet which releases an initial burst of therapeutic agent and thereafter releases the agent at an essentially constant rate comprising an acid soluble therapeutic agent in an insoluble matrix, the tablet containing an acid insoluble, base soluble pharmaceutically acceptable component selected from polymers and fatty acids, a pharmaceutically acceptable, organic acid and at least one pharmaceutically acceptable excipient, the component and the acid each being present in an amount of from about 1–25 percent by weight of total composition.

The tablet is preferred wherein the component is a polymeric acid phthalate and the acid is a mono- or polycarboxylic acid, especially wherein the component is hydroxypropyl methylcellulose phthalate and the acid is citric acid.

The tablet is also preferred wherein the component is present in an amount of from 3–15 percent by weight and the acid is present in an amount of from about 7–20 percent by weight, both based on the weight of the total composition. In one preferred form, the therapeutic agent is trimazosin and the excipient is selected from ethyl cellulose, hydrogenated vegetable oil and mixtures thereof.

In its most preferred form, the tablet comprises about 40–60 weight % trimazosin, about 4–5 weight % ethyl cellulose, about 12–15 weight percent citric acid and about 3–7 weight percent hydroxypropyl methylcellulose phthalate. Another preferred form of the tablet also contains from about 7–8 weight percent zein, based on the weight of the total composition.

DETAILED DESCRIPTION OF THE INVENTION

As to therapeutic agents suitable for use with the matrix tablet formulations of this invention, any acid-soluble therapeutic agent can be used, but of course those agents wherein a constant blood level is required over a sustained period of time will be chosen. The preferred agent of this invention is trimazosin which is acid soluble and wherein, because of its anti-hypertensive utility, a constant blood level is required for maximum patient benefit. The matrix formulation of this invention will allow once-a-day dosing which is an advance over the many multiple daily dose agents now available as well as over the multiple daily dosage form of trimazosin. Other therapeutic agents which require a long-term constant blood level, such as agents for any chronic condition, would be useful in this formulation. Agents such as the bronchodilator theophylline, among many others, would be suitable for incorporation into these formulations. The therapeutic agent will usually be employed in an amount of from about 25–75 percent by weight and preferably from about 40–60 percent by weight of total composition.

As to the acid insoluble, base soluble component of the formulations of this invention, pharmaceutically acceptable polymers and fatty acids are useful. Such polymers as polymeric acid phthalates, particularly hydroxypropyl methylcellulose phthalate, are preferred but numerous other polymers can be employed including copolymers of methacrylic acid and methacrylic acid methyl ester.

The function of this component is readily apparent to those skilled in the art; it protects the tablet in the acid environment of the stomach, allowing an initial burst of agent but preventing disintegration of the tablet and dumping of the entire dose at once. It also solubilizes slowly in the basic environment of the gut allowing a constant rate of release over a controlled period of time in order to maintain the desired blood level of therapeutic agent. This component will usually be employed in an amount of about 3–15 percent by weight and preferably about 3–7 percent by weight of total composition.

The acids useful in the present matrix tablet formulation are mono- and polycarboxylic acids. It will be apparent to those skilled in the art that the function of the acid is to provide an acid microenvironment for the acid soluble therapeutic agent in the basic macroenvironment of the gut. Without this acid, the agent would be essentially insoluble and the only dose available to the patient would be the initial burst in the stomach.

The preferred acid is citric acid but numerous other mono- and polycarboxylic acids will function well, so long as they are pharmaceutically acceptable. Such acids include benzenesulfonic, fumaric, ethylenediamine tetraacetic, ethanesulfonic, ethanedisulfonic, laurylsulfonic, glucoheptonic, gluconic, glutamic, maleic, mandelic, methane sulfonic, succinic, hydroxyethanesulfonic, aspartic, glycerophosphoric and lactic acids.

The acid selected will usually be employed in an amount of from about 7-20 percent by weight and preferably from about 12-15 percent by weight of total composition.

The function of the pharmaceutically acceptable excipients is the normal function in a tablet; i.e. they bind or hold together the other materials. A wide variety of excipients can be employed including copolymers of acrylic and methacrylic acid esters with a low content of quaternary ammonium groups; gelatin; natural gums; starches and modified starches; alginates; microcrystalline cellulose and cellulose derivatives; waxes; fats; mono- di- and tri-glycerides of fatty acids and fatty acid esters; and acetylated monoglycerides but ethyl cellulose, hydrogenated vegetable oil or mixtures of the two are preferred.

The one or more excipients used will be employed in a total amount of from about 2-10 percent by weight and preferably from about 4-5 percent by weight of total composition.

An additional ingredient, zein, is often preferred in these formulations and when it is used it will be employed in a range of from about 5-10 percent by weight, preferably from about 7-8 percent by weight of total composition.

Typically in the manufacture of the matrix tablets of this invention the therapeutic agent will be blended with one or more excipients, the acid insoluble, base soluble component and optionally zein for several minutes. The blend (A) may be milled and is then set aside. Then additional excipient and component are blended. To this second blend (B) ethanol is slowly added with stirring to form a paste which is allowed to stand for about 5 to 60 minutes and is then mixed again before using. A and B above are blended adding some alcohol if necessary to form a dough. Calcium silicate or other granulation and drying aids may be added to the dough and the whole is mixed until it becomes granular. The granules are air dried at about 50° C. and are then milled to the desired size. These granules are designated the active granules and are set aside.

In a second step, citric acid, excipients, the component and optionally zein are blended for several minutes and then milled and further blended. Ethanol is mixed with the blend to form a dough and calcium silicate or other solvent sorbing excipient is added to the dough with mixing. The mixing is continued until small spheres form and these spheres are hot air dried and milled to the desired size. These granules are designated the citric granules and are set aside.

In a third step the active granules and the citric granules are blended for several minutes and are then further blended with magnesium stearate or other lubricants if desired. This granulation is tableted into the matrix tablets of this invention.

Plasma levels were tested in order to establish the efficacy of the long-acting formulations of this invention. Mean trimazosin plasma levels from 19 subjects given 300 mg long-acting tablets in a crossover bioavailability study with 100 mg standard tablet tid are as follows:

| Hrs Post Dose | Plasma level (mcg/ml) | Hrs Post Dose | Plasma level (mcg/ml) | Hrs Post Dose | Plasma level (mcg/ml) |
| --- | --- | --- | --- | --- | --- |
| 0.5 | 3.0 | 8.0 | 4.6 | 16.0 | 2.3 |
| 1.0 | 4.5 | 8.5 | 4.9 | 16.5 | 1.9 |
| 2.0 | 5.5 | 9.0 | 4.9 | 17.0 | 1.8 |
| 4.0 | 5.9 | 10.0 | 4.8 | 18.0 | 1.5 |
| 6.0 | 5.5 | 12.0 | 4.2 | 24.0 | 0.7 |

Plasma levels for the standard tablet peaked about 1 hour post dose and showed steadily declining levels thereafter with a terminal half life of 4.3 hours.

The following examples are illustrative and in no way limit the scope of the claims to follow.

EXAMPLE 1

Composition of Active Granulation

| Component | Weight mg |
| --- | --- |
| Trimazosin HCl | 680.344 |
| Hydrogenated Vegetable Oil | 40.070 |
| Ethylcellulose | 10.016 |
| Zein | 15.967 |
| Hydroxypropyl Methylcellulose Phthalate | 9.980 |
| Ethylcellulose | 40.070 |
| Zein | 63.875 |
| Hydroxypropyl Methylcellulose Phthalate | 39.930 |
| Ethanol (volatile) | (317.660) |
| Calcium Silicate | 99.748 |
| Total | 1000.000 |

MANUFACTURING INSTRUCTIONS: ACTIVE GRANULATION

1. Combine the trimazosin HCl, hydrogenated vegetable oil, the first portions of ethylcellulose, zein and hydroxypropyl methylcellulose phthalate in an appropriate size blender and blend for 15 minutes.
2. Pass the blend through a mill at slow speed, blend for 30 minutes and hold.
3. Combine the remaining portion of ethylcellulose, zein and hydroxypropyl methylcellulose phthalate and blend for 15 minutes.
4. Slowly add the blend from step 3 to an appropriate vessel containing an amount of ethanol to form a 45% w/w solution and stir until solution (paste) is formed. Cover the solution and allow to stand for about 60 minutes; stir before using.
5. Charge an appropriate size kettle with the dry blend from step 2, and while mixing add the granulating solution from step 4 and mix until uniformly wet, about 10 minutes.
6. With continued mixing slowly add the calcium silicate to the wet material in step 5 and continue mixing until granular, about 6 minutes. Additional ethanol may be added to obtain proper consistency (small spheres should start to form).
7. Spread the granulation on polyethylene lined trays and dry in a forced hot air dryer at about 50° C. until material is suitable for milling (approx. 16 hours).
8. After the proper conditions are attained mill the partially dried material at slow speed.
9. Spread the material on polyethylene lined trays and place in dryer at 50° C. to complete the drying phase (about 16 hours).
10. Once dried, blend the granulation briefly and hold.

Composition of Citric Acid Granulation

| Component | Weight mg |
|---|---|
| Citric Acid Powder | 767.190 |
| Hydrogenated Vegetable Oil | 29.197 |
| Ethylcellulose | 36.482 |
| Zein | 58.148 |
| Hydroxypropyl Methylcellulose Phthalate | 36.346 |
| Ethanol (volatile) | (231.36) |
| Calcium Silicate | 72.637 |
| Total | 1000.000 |

MANUFACTURING INSTRUCTIONS

1. Combine the citric acid, hydrogenated vegetable oil, ethylcellulose, zein and hydroxypropyl methylcellulose phthalate in an appropriate size blender and blend for 15 minutes.
2. Pass the blend from step 1 through a mill at slow speed.
3. Blend for 30 minutes.
4. Charge an appropriate size kettle with the blend from step 3 and while mixing add the ethanol slowly until material forms a dough-like consistency.
5. To the wet material add the calcium silicate, a third at a time, mixing between additions.
6. Continue mixing until small, granular spheres form, adding additional ethanol if necessary.
7. Spread the granulation on polyethylene lined trays and dry in a forced air oven at about 50° C. for 16 hours.
8. Mill the dried granulation through at slow speed.
9. Blend for 30 minutes.
10. Return the granulation to the dryer for an additional 16 hours of drying at 50° C. and hold.

Composition of Long Acting Tablets

| Component | Weight mg |
|---|---|
| Active Granulation | 496.011 |
| Citric Acid Granulation | 109.944 |
| Artificial Flavor | 6.090 |
| Magnesium Stearate | 3.060 |

MANUFACTURING INSTRUCTIONS

1. Combine the active granulation, the citric acid granulation and the artificial flavor and blend for 20 minutes.
2. Add the Magnesium Stearate to the blend from step 1 and blend for 5 minutes.
3. Tablet the granulation.

The dissolution time for a 300 mg tablet was tested by immersing the tablet in simulated gastric fluid without enzymes for one hour followed by immersion in simulated intestinal fluid also without enzymes. The results are as follows:

| Hours | 1 | 3 | 5 | 7 | 9 |
|---|---|---|---|---|---|
| % Dissolution | 16 | 28 | 48 | — | 76 |

EXAMPLE 2

Long Acting Tablets

| | |
|---|---|
| Trimazosin HCl | 11.738 g |
| Citric Acid | 2.934 g |
| Hydrogenated Vegetable Oil | 3.728 g |
| Zein | 1.600 g |
| Hydroxypropyl Methylcellulose Phthalate | 1.000 g |
| Calcium Silicate | 2.000 g |
| Ethanol (volatile) | (4.830 g) |
| | 23.000 g |

Procedure:
1. Add the zein and hydroxypropyl methylcellulose phthalate to the ethanol while mixing. Let the solution stand for about 60 minutes.
2. Blend the trimazosin hydrochloride, citric acid and hydrogenated vegetable oil together.
3. Add the blend from step 2 to the solution from step 1 and mix well.
4. Add the calcium silicate to the mixture from step 3 and blend until granular.
5. Dry the granulation overnight in a 50° C. forced hot air oven.
6. Screen the dried granulation.
7. Tablet the granulation into 100 mg tablets.

The dissolution time was again tested as in Example 1 and the results obtained were as follows:

| Hours | 1 | 3 | 5 | 7 | 9 |
|---|---|---|---|---|---|
| % Dissolution | 15 | 32 | 54 | — | 70 |

EXAMPLE 3

Composition of Citric Granulation

| Component | Weight |
|---|---|
| 1. Citric Acid | 230.1570 g |
| 2. Hydrogenated Vegetable Oil | 8.7591 g |
| 3. Ethylcellulose | 10.9446 g |
| 4. Hydroxypropyl Methycellulose Phthalate | 10.9038 g |
| 5. Calcium Silicate | 21.7911 g |

MANUFACTURING INSTRUCTIONS

1. Combine items 1–4 and blend well for 5 minutes.
2. Mill blend at slow speed.
3. Put blend from step 2 in mixer.
4. Mix on slow speed, slowly add 47.3 g ethanol, mixing for 7 minutes until dough ball forms.
5. Add ⅓ of calcium silicate and mix for 4 minutes and then add 4.8 g ethanol to settle dust.
6. Add second ⅓ of calcium silicate and mix for 3 minutes.
7. Add last ⅓ of calcium silicate and mix for 8 minutes adding 1.4 g ethanol to settle dust.
8. Spread on poly bag covered tray and place in 50° C. forced hot air oven.
9. Mill at slow speed.
10. Return to oven for additional 16 hours.

Composition of Active Granulation

| Component | Weight |
| --- | --- |
| 1. Trimazosin HCl | 244.9 g |
| 2. Hydrogenated Vegetable Oil | 14.4 g |
| 3. Ethylcellulose | 12.6 g |
| 4. Hydroxypropyl Methycellulose | 12.6 g |
| 5. Ethylcellulose | 5.4 g |
| 6. Hydroxypropyl Methycellulose Phthalate | 5.4 g |
| 7. Calcium Silicate | 35.9 g |

MANUFACTURING INSTRUCTIONS

1. Combine items 1-4 and blend well for 5 minutes.
2. Mill blend at slow speed.
3. Place polymers (items 5 and 6) in 13.2 g ethanol and allow to solvate for 5 minutes.
4. Add blend from step 2 and mix for 2 minutes adding 91.6 g ethanol; dough ball forms.
5. Add ⅓ calcium silicate and mix for 5 minutes. Add 12.1 g ethanol to settle dust.
6. Add second ⅓ calcium silicate and mix for 5 minutes. Add 20.8 g ethanol.
7. Add last ⅓ calcium silicate and mix for 5 minutes. Add 39.6 g ethanol to settle dust.
8. Spread on poly bag covered tray and place in 50° C. oven for 16 hours.
9. Mill at slow speed.
10. Return to oven for additional 16 hours.

Composition of Long Acting Tablets

| Component | Weight |
| --- | --- |
| 1. Active granulation | 311.1 g |
| 2. Citric granulation | 69.0 g |
| 3. Magnesium stearate | 1.9 g |

1. Combine all 3 items and blend for 5 minutes.
2. Tablet on press for 150 mg tablets.

The dissolution time was tested by immersing the tablet in water for 1 hour followed by immersion in similated intestinal fluid without enzymes, and the results were as follows:

| Hours | 1 | 3 | 5 | 7 | 9 |
| --- | --- | --- | --- | --- | --- |
| % Dissolution | 32 | 48 | 61 | 69 | 77 |

EXAMPLE 4

Composition of Theophylline Long Acting Tablet

| Component | Weight (mg/tablet) |
| --- | --- |
| 1. Theophylline | 300.00 |
| 2. Citric Acid | 75.07 |
| 3. Hydrogenated Vegetable Oil | 20.55 |
| 4. Ethylcellulose | 25.61 |
| 5. Zein | 40.94 |
| 6. Hydroxypropyl Methycellulose Phthalate | 25.59 |
| 7. Ethanol (volatile) | (163.00) |
| 8. Calcium Silicate | 51.14 |
| 9. Magnesium Stearate | 2.72 |

MANUFACTURING INSTRUCTIONS

1. Add items 1-6 to mixer and mix for approximately fifteen minutes.
2. While mixing add the Ethanol (item 7) until evenly wet.
3. With continued mixing slowly add the Calcium Silicate to the wet material in step 2 and continue mixing until mass becomes granular.
4. Dry material.
5. Mill the material at slow speed.
6. Dry the sized material.
7. Combine the magnesium stearate with a portion of the granulation. Mix thoroughly and incorporate into remaining granulation of step 6.
8. Blend material in suitable blender for 5 minutes.
9. Compress tablets on tablet press.

The dissolution time was tested as in Example 1 and the following results were obtained:

| Hours | 1 | 2 | 5 | 8 | 10 |
| --- | --- | --- | --- | --- | --- |
| % Dissolution | 18 | 25 | 38 | 50 | 67 |

EXAMPLE 5

Composition of Long Acting Tablet

| Component | Weight (g) |
| --- | --- |
| Trimazosin HCl | 112.486 |
| Fumaric Acid | 15.208 |
| Hydrogenated Vegetable Oil | 7.695 |
| Ethylcellulose | 9.618 |
| Zein | 15.332 |
| Hydroxypropyl Methylcellulose Phthalate | 9.584 |
| Calcium Silicate | 19.167 |
| Magnesium Stearate | 1.010 |
|  | 190.100 |

MANUFACTURING PROCEDURE

1. Blend first 6 ingredients for 10 minutes.
2. Mill the blend at slow speed.
3. Add 100 ml ethanol to the blend with mixing until uniformly wet.
4. Add the Calcium silicate to the wet mass, mix until granular, then dry.
5. Mill the granulation at slow speed and complete drying.
6. Add Magnesium stearate to the granulation and blend for 5 minutes.
7. Compress into 100 mg tablets in a tablet press.

The dissolution time was tested as in Example 1 and the following results were obtained:

| Hours | 1 | 3 | 5 | 7 | 9 |
| --- | --- | --- | --- | --- | --- |
| % Dissolution | 14 | 50 | 78 | — | 88 |

EXAMPLE 6

Composition of Active Granulation

| Component | Weight (mg per tablet) |
| --- | --- |
| 1. Trimazosin HCl | 168.7290 |
| 2. Hydrogenated Vegetable Oil | 9.9375 |

-continued

| Component | Weight (mg per tablet) |
|---|---|
| 3. Hydroxypropyl Methylcellulose Phthalate | 44.6010 |
| 4. Calcium Silicate | 24.7380 |

MANUFACTURING INSTRUCTIONS

1. Combine ingredients 1,2 and a portion of 3 and mix slowly.
2. Add ethanol to remainder of item 3 with mixing.
3. Add solution from step 2 to blend from step 1 with mixing to form a dough.
4. Add calcium silicate in 3 equal batches with ethanol to form a stiff dough.
5. Dry in 50° C. dryer.
6. Mill, redry, blend and hold.

Composition of Citric Granulation

| Component | Weight (mg per tablet) |
|---|---|
| Citric Acid | 42.1740 |
| Hydrogenated Vegetable Oil | 1.6050 |
| Hydroxypropyl Methylcellulose Phthalate | 7.2000 |
| Calcium Silicate | 3.9930 |

MANUFACTURING INSTRUCTIONS

1. Combine first three ingredients and mill at slow speed.
2. Add ethanol and blend to form a dough.
3. Add calcium silicate in three batches with ethanol to form a stiff dough.
4. Dry, mill, redry, blend and hold.

Composition of Long Acting Tablets

| Component | Weight |
|---|---|
| Active Granulation | 354.3 g |
| Citric Granulation | 78.5 g |
| Magnesium Stearate | 2.2 g |

1. Combine the two granulations and blend.
2. Add the magnesium stearate and blend.
3. Tablet the mixture on a press to form 150 mg tablets.
   Using the method of Example 3, dissolution rate was tested and the following results were obtained:

| Hours | 1 | 3 | 5 | 7 | 9 |
|---|---|---|---|---|---|
| % Dissolution | 27 | 44 | 78 | 100 | 100 |

EXAMPLE 7

Composition of Citric Granulation

| Component | Weight (g) |
|---|---|
| Dry Portion | |
| Citric Acid | 281.160 |
| Hydrogenated Vegetable Oil | 10.700 |
| Ethylcellulose | 2.670 |
| Zein | 4.260 |
| Hydroxypropyl Methylcellulose Phthalate | 2.660 |
| | 301.450 |
| Solution | |

-continued

| Component | Weight (g) |
|---|---|
| Ethylcellulose | 10.700 |
| Zein | 17.050 |
| Hydroxypropyl Methylcellulose Phthalate | 10.660 |
| Ethanol (volatile) | (84.790) |
| Calcium Silicate | 26.620 |

MANUFACTURING INSTRUCTIONS

1. Blend all ingredients for dry portion at slow speed and mill.
2. Stir the dry ingredients for the solution into the ethanol, allow to stand one hour and stir again.
3. While mixing add the solution from 2 to the dry blend from 1 and mix until dough forms.
4. With continued mixing, add the Calcium Silicate and mix about 10 minutes.
5. Dry at 50° C.
6. Mill the granulation at slow speed.
7. Redry the granulation at 50° C.
8. Remill and hold.

Active Granulation

| Component | Weight (g) |
|---|---|
| Dry Portion | |
| Trimazosin HCl | 449.944 |
| Hydrogenated Vegetable Oil | 25.500 |
| Ethylcellulose | 6.624 |
| Zein | 10.560 |
| Hydroxypropyl Methylcellulose Phthalate | 6.600 |
| | 499.228 |
| Solution | |
| Ethylcellulose | 26.500 |
| Zein | 42.244 |
| Hydroxypropyl Methylcellulose Phthalate | 26.408 |
| Ethanol (volatile) | (210.084) |
| Calcium Silicate | 65.968 |

MANUFACTURING INSTRUCTIONS

1. Blend all of the dry portion and mill at slow speed.
2. Blend the dry ingredients for the solution and stir them into ethanol. Allow to stand one hour and stir.
3. Blend the 1 and 2 until dough-like and with continued mixing add calcium silicate. Mix about 10 minutes.
4. Dry at 50° C.
5. Mill the granulation at slow speed and hold.

Composition of Long Acting Tablets

| Component | Weight (g) |
|---|---|
| Active Granulation | 165.337 |
| Citric Granulation | 15.934 |
| Magnesium Stearate | 0.906 |

MANUFACTURING INSTRUCTIONS

1. Combine the two granulations and blend for 10 minutes.
2. Add the magnesium stearate and blend for 5 minutes.
3. Tablet into 100 mg tablets with a tablet press.
   Following the method of Example 1, dissolution rate was tested and the following results were obtained:

| Hours | 1 | 3 | 5 | 7 | 9 |
|---|---|---|---|---|---|
| % Dissolution | 19 | 28 | 37 | — | 62 |

EXAMPLE 8

Composition of Active Granulation

| Component | Weight (g) |
|---|---|
| 1. Trimazosin HCl | 1700.7 |
| 2. Hydrogenated Vegetable Oil | 100.3 |
| 3. Ethylcellulose | 87.8 |
| 4. Zein | 139.6 |
| 5. Hydroxypropyl Methylcellulose Phthalate | 87.2 |
| 6. Ethylcellulose | 37.5 |
| 7. Zein | 60.1 |
| 8. Hydroxypropyl Methylcellulose Phthalate | 37.5 |
| 9. Calcium Silicate | 249.3 |

MANUFACTURING INSTRUCTIONS

1. Combine components 1–5, blend and mill at slow speed.
2. Blend components 6–8 and mix with 46.2 g ethanol.
3. Blend 1 and 2 with additional ethanol to form a dough.
4. Add calcium silicate in 3 parts and mix for 15 minutes.
5. Dry, mill at slow speed, dry and hold.

Composition of Citric Granulation

| Component | Weight (g) |
|---|---|
| 1. Citric Acid | 1841.2 |
| 2. Hydrogenated Vegetable Oil | 70.0 |
| 3. Ethylcellulose | 87.6 |
| 4. Zein | 139.6 |
| 5. Hydroxypropyl Methylcellulose Phthalate | 87.2 |
| 6. Calcium Silicate | 174.4 |

MANUFACTURING INSTRUCTIONS

1. Blend components 1–5 and mill at slow speed.
2. Mix the blend with ethanol until a dough forms.
3. Add calcium silicate in 3 parts with mixing and with additional ethanol to keep dust down.
4. Dry, mill, dry and hold.

Composition of Long Acting Tablets

| Component | Weight (g) |
|---|---|
| Active Granulation | 320.00 |
| Citric Granulation | 99.30 |
| Artifical Flavor | 3.92 |
| Magnesium Stearate | 2.12 |

MANUFACTURING INSTRUCTIONS

1. Combine first 3 ingredients and blend for 5 minutes.
2. Add magnesium stearate and blend for additional 5 minutes.
3. Tablet into 300 mg tablets on a tablet press.

Using the method of Example 3 the tablets were tested for dissolution rate and the following results were obtained:

| Hours | 1 | 3 | 5 | 7 | 9 |
|---|---|---|---|---|---|
| % Dissolution | 25 | 36 | 48 | 71 | 82 |

We claim:

1. A pharmaceutical tablet which releases an initial burst of therapeutic agent and thereafter releases said agent at an essentially constant rate comprising an acid-soluble therapeutic agent, an acid-insoluble, base-soluble pharmaceutically acceptable polymeric acid phthalate, and a pharmaceutically acceptable polycarboxylic acid in an insoluble matrix consisting of ethyl cellulose, hydrogenated vegetable oil or mixtures thereof, said phthalate being present in an amount of from about 1 to 25 percent by weight of said tablet, said acid being present in an amount of from about 7 to 20% by weight of said tablet, said matrix components being present in an amount of from about 2–10% by weight of said tablet and said therapeutic agent being present in an amount of from about 25–75% by weight of said tablet.

2. The tablet of claim 1 wherein said phthalate is hydroxypropyl methylcellulose phthalate and said acid is citric acid.

3. The tablet of claim 2 wherein said phthalate is present in an amount of from 3–15 percent by weight.

4. The tablet of claim 1 wherein said therapeutic agent is trimazosin.

5. The tablet of claim 1 comprising about 40–60 weight % trimazosin, about 4–5 weight % ethyl cellulose, about 12–15 weight % citric acid and about 3–7 weight percent hydroxypropyl methylcellulose phthalate.

6. The tablet of claim 5 which also contains from about 7–8 weight percent zein.

* * * * *